United States Patent
Yang

(10) Patent No.: US 8,173,172 B2
(45) Date of Patent: *May 8, 2012

(54) PREPARATION OF POWDER AGGLOMERATES

(75) Inventor: Tsong-Toh Yang, Warren, NJ (US)

(73) Assignee: Schering Corporation, Kenilworth, NJ (US)

( * ) Notice: Subject to any disclaimer, the term of this patent is extended or adjusted under 35 U.S.C. 154(b) by 20 days.

This patent is subject to a terminal disclaimer.

(21) Appl. No.: 11/947,608

(22) Filed: Nov. 29, 2007

(65) Prior Publication Data

US 2008/0118566 A1 May 22, 2008

Related U.S. Application Data

(63) Continuation of application No. 10/725,845, filed on Dec. 2, 2003, now abandoned, which is a continuation of application No. 10/238,423, filed on Sep. 10, 2002, now abandoned, which is a continuation of application No. 09/901,205, filed on Jul. 9, 2001, now Pat. No. 6,495,167, which is a continuation of application No. 09/824,377, filed on Apr. 2, 2001, now Pat. No. 6,503,537, which is a continuation of application No. 09/042,973, filed on Mar. 17, 1998, now abandoned.

(60) Provisional application No. 60/041,055, filed on Mar. 20, 1997.

(51) Int. Cl.
*A61K 9/14* (2006.01)

(52) U.S. Cl. ......... 424/491; 424/489; 424/493; 424/497

(58) Field of Classification Search ........................ None
See application file for complete search history.

(56) References Cited

U.S. PATENT DOCUMENTS

| | | |
|---|---|---|
| 4,161,516 A | 7/1979 | Bell |
| 4,472,393 A | 9/1984 | Shapiro |
| 5,143,126 A | 9/1992 | Boesch et al. |
| 5,229,422 A | 7/1993 | Takahashi et al. |
| 5,474,759 A | 12/1995 | Fassberg et al. |
| 5,551,489 A | 9/1996 | Trofast et al. |
| 5,562,923 A | 10/1996 | Trofast et al. |
| 5,637,620 A | 6/1997 | Trofast et al. |
| 5,642,728 A | 7/1997 | Andersson et al. |
| 5,709,884 A | 1/1998 | Trofast et al. |

(Continued)

FOREIGN PATENT DOCUMENTS

EP 0 291 201 11/1988

(Continued)

OTHER PUBLICATIONS

H.J. Lee et al., "Anti-Inflammatory Steroids: Research Trends and New Compounds", Drugs of Today, vol. 25, pp. 577-588 (1989).

M. Angberg et al, "Evaluation of Heat-Conduction Microcalorimetry in Pharmaceutical Stability Studies. III. Crystallographic Changes Due to Water Vapour Uptake in Anhydrous Lactose Powder", International Journal of Pharmaceutics, vol. 73, pp. 209-200 (1991).

(Continued)

*Primary Examiner* — Bethany Barham

(74) *Attorney, Agent, or Firm* — Matthew A. Leff; Valerie J. Camara

(57) ABSTRACT

The invention relates to a method of producing an agglomerate of drug and solid binder. The process involves producing individual agglomerate particles and then converting the convertible amorphous content of same, following agglomeration, by the application of, for example, moisture. Agglomerates capable of conversion as well as the finished agglomerates and oral and nasal dosing systems including same are also contemplated. The process produces agglomerates which are rugged but which will produce an acceptable fine particle fraction during dosing.

25 Claims, 4 Drawing Sheets

U.S. PATENT DOCUMENTS

Figure 1:
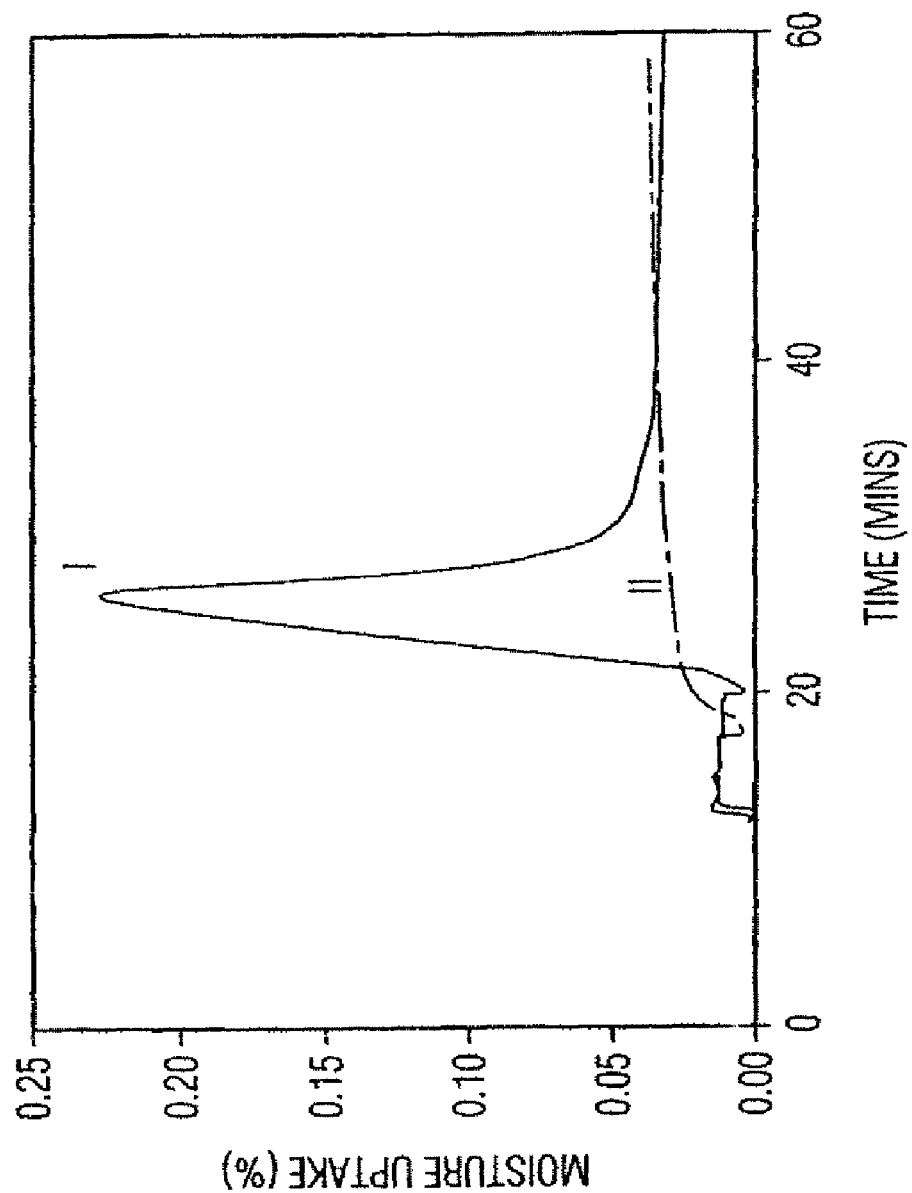

| | | | |
|---|---|---|---|
| 5,837,699 A * | 11/1998 | Sequeira et al. | 514/169 |
| 5,874,063 A * | 2/1999 | Briggner et al. | 424/45 |
| 5,934,273 A | 8/1999 | Andersson et al. | |
| 5,980,949 A | 11/1999 | Trofast | |
| 5,983,956 A | 11/1999 | Trofast | |
| 6,030,604 A | 2/2000 | Trofast | |
| 6,183,782 B1 | 2/2001 | Hallworth | |
| 6,250,300 B1 | 6/2001 | Andersson et al. | |
| 6,371,171 B1 * | 4/2002 | Trofast et al. | 141/1 |

FOREIGN PATENT DOCUMENTS

| | | |
|---|---|---|
| EP | 0 441 740 | 8/1991 |
| EP | 0 518 600 | 12/1992 |
| GB | 1 520 247 | 8/1978 |
| WO | WO 94/13271 | 6/1994 |
| WO | WO 94/14492 | 7/1994 |
| WO | WO 95/05805 | 3/1995 |
| WO | WO 95/09615 | 4/1995 |
| WO | WO 95/09616 | 4/1995 |
| WO | WO 95/10407 | 4/1995 |
| WO | WO 95/20393 | 8/1995 |
| WO | WO 96/19206 | 6/1996 |

OTHER PUBLICATIONS

T. Sebhatu et al., "Assessment of the Degree of Disorder in Crystalline Solids by Isothermal Microcalorimetry", International Journal of Pharmaceutics, vol. 104, pp. 135-144 (1994).

L.E. Briggner et al., "The Use of Isothermal Microcalorimetry in the Study of Changes in Crystallinity Induced During the Processing of Powders", International Journal of Pharmaceutics, vol. 105, pp. 125-135 (1994).

T. Sebhatu et al., "Effect of Moisture Sorption on Tabletting Characteristics of Spray Dried (15% Amorphous) Lactose", Pharmaceutical Research, vol. 11, pp. 1233-1238 (1994).

G. Buckton et al., "The Influence of Additives on the Recrystallization of Amorphous Spray Dried Lactose", International Journal of Pharmaceutics, vol. 121, pp. 81-87 (1995).

B.C. Hancock et al., "Molecular Mobility of Amorphous Pharmaceutical Solids Below Their Glass Transition Temperature", Pharmaceutical Research, vol. 12, pp. 799-806, 1995.

* cited by examiner

PREPARATION OF POWDER AGGLOMERATES

CROSS-REFERENCE TO RELATED APPLICATIONS

This application is a continuation of U.S. patent application Ser. No. 10/725,845, filed Dec. 2, 2003, which is a continuation of U.S. patent application Ser. No. 10/238,423, filed Sep. 10, 2002, now abandoned, which is a continuation of U.S patent application Ser. No. 09/901,205, filed Jul. 9, 2001, now issued as U.S. Pat. No. 6,495,167, which is a continuation of U.S. patent application Ser. No. 09/824,377, filed Apr. 2, 2001, now issued as U.S. Pat. No. 6,503,537, which is a continuation of U.S. patent application Ser. No. 09/042,973, filed Mar. 17, 1998, now abandoned, which claimed benefit of priority to U.S. Provisional Application Ser. No. 60/041,055, filed Mar. 20, 1997, expired. Benefit of priority to all of said applications is hereby formally claimed.

BACKGROUND OF THE INVENTION

The present invention relates broadly to the formation of agglomerates. More specifically, the present invention relates to the field of pharmaceutical dosage form design and, in particular, the production of unique agglomerated dosage forms for administration of pharmacologically active agents to patients. The formulations in accordance with this invention are particularly well suited for oral and/or nasal inhalation.

INTRODUCTION TO THE INVENTION

There are several known methods of treating diseases and conditions of the upper and lower airway passages and the lungs. These conditions include, for example, asthma and rhinitis. One such technique involves administering certain pharmacologically active agents or drugs such as, for example, mometasone furoate, topically to the airway passages or lungs in an immediately useable form. Mometasone furoate is a topically effective, steroidal anti-inflammatory.

Oral inhalation therapy is one method of delivering such topically active drugs. This form of drug delivery involves the oral administration of a dry powdered drug directly to the afflicted area in a form which is readily available for immediate benefit.

However, inhalation therapy is a particularly demanding dosing system and it involves its own set of unique design and performance problems. Amongst those problems is a concern over the accuracy and repeatability of dosing. One must try to ensure that the same amount of drug is administered each and every time. Moreover, unlike pills, capsules and creams, oral inhalation therapy must concern itself with not only the dosage form itself, but also a drug delivery device and the interaction between them. One has only to consider over-the-under nasal sprays to understand this problem. When one squeezes a conventional squeeze bottle, it is difficult to apply the same amount of force each and every time. With even a slight difference in force, differences in the amount of drug administered can result. Even with somewhat more consistent pump style spray applicators, variations in dosing can occur. While such variation is usually not a problem when administering OTC nasal sprays, variation should be minimized where possible when administering prescription medications for such serious conditions as asthma. The dangers of over-medicating or under-medicating and the consequences of such unwanted deviation can be profound. The problem becomes even more complex when the size of the doses are as small as they often are in oral inhalation therapy.

To help mitigate these problems, companies such as Schering Corporation have developed complex and highly accurate inhaler systems for administering powdered medications such as those described in PCT International Publication No. WO 94/14492, which was published on Jul. 7, 1994, the text of which is hereby incorporated by reference. Such inhaler systems were designed to meter out an exact dose of a powdered medication using a dosing hole of a specific size. The hole is completely filled with drug prior to administration and the entire contents of the dosing hole are then delivered to the patient through a nozzle. The dosing hole is then filled again for the next dose. These devices have been specifically designed to remove, as much as possible, human error and mechanically induced variability in dosing.

While such devices represent a significant advance in oral inhalation therapy, there are still some circumstances in which problems may remain. These problems often center on the properties of the pharmacologically active agent and their interaction with the inhaler. For example, certain drugs are not "free-flowing" and that may make it difficult to move the drug from storage in a reservoir, to measurement in a dosing hole, to delivery from the inhaler. Other drugs may suffer from electrostatic charge problems or may exhibit an unacceptable degree of cohesive force. Such drugs may be "sticky," even when in powdered form. These drugs may clog the inhaler/applicator, affecting its ability to properly meter the intended amount of medication. Such powders may also adhere to the nozzle of the applicator, thus reducing the amount of medication actually delivered. This is often referred to as "hang up." Drugs may also be "fluffy" which makes handling and loading sufficient drug into a dosing hole a real challenge. To make matters even worse, these and other physical properties of various pharmacologically active agents may vary within a single batch of material. This can defeat attempts to compensate.

Related problems may also result based upon the small size of the particles which are generally used in inhalation therapy. Inhalation therapy commonly involves drug particles which are on the order of 10 μm or below. This ensures adequate penetration of the medicament into the lungs of the patient as well as good topical coverage. In order to provide adequate dispensing of such medicines, tight control must be maintained on the size of the particles of the drug. However, powders of this size can be extremely difficult to work with, particularly when small dosages are required. Such powders are typically not free-flowing and are usually light, dusty or fluffy in character, creating problems during handling, processing, and storing. In addition, it can be difficult to repeatedly and accurately load such materials into the dosing hole of an inhaler. Thus not only the properties of the drug, but also the required size of the therapeutic particulate, can combine to cause considerable problems in terms of handling and dosing.

One method of improving the ability to administer fine powdered medicaments is by the inclusion of dry excipients such as, for example, dry lactose. However, it has been determined that when particularly small doses of medication are required, such as under about 100-200 μg of drug, the inclusion of conventional excipients may not adequately compensate for the problems associated with the use of fine drug particles. In addition, dry excipients as commonly used, generally have particle sizes which are significantly larger than the particle size of the drug. Unfortunately, the use of such large particles can have a significant impact on the amount of drug delivered from dose to dose. Moreover, the intended benefits of the use of such excipients begins to diminish as the size of the dose decreases. Therefore, drug hang up or retention within the metering device or the inhalation nozzle and other handling issues can become an increasing problem.

Alternatively, drug products can be processed to form agglomerates or pellets which are generally more free-flowing and bulky. One method of agglomerating drugs is described in PCT International Publication No. WO 95/09616, published on Apr. 13, 1995. As described therein, agglomerates of finely divided powder medicaments, such as micronized powders having a particle size smaller than 10 μm, can be produced which require no binders. However, they can be formed with excipients. These agglomerates can then be administered through an inhaler for powdered medications.

The ability to create particles without a binder is significant to inhalation therapy and can pose a great advantage over other techniques which use water or other traditional binders in agglomerate formation. Agglomerates of pure drug can provide great advantages when formulating and handling powders. It has been found, however, that at doses of about 100-200 μg, of a drug such as mometasone furoate, and below, agglomerates of pure drug can suffer from hang up and dosing variability can be a genuine concern. Even in dosing systems designed to provide relatively larger doses of pharmacologically active agent, such as about 400 μg or above, the resulting agglomerates of pure drug can still suffer from integrity problems. These agglomerates are still relatively soft and can be crushed during metering thereby providing variability in dosing. The material can also be broken fairly readily by, for example, dropping an inhaler from a height of about four feet. This would prematurely result in the formation of smaller particles which are more difficult to handle. In fact, it is the handling difficulties of the fine drug particles that necessitated agglomeration in the first place.

If binder-containing agglomerates are to be used, such agglomerates can be made by the methods described in, for example, U.S. Pat. No. 4,161,516 and GB Patent 1,520,247 which disclose the use of certain binding materials, including water, for the production of agglomerates for oral inhalation. According to the processes described therein, prior to agglomeration, the moisture content of certain "self agglomerating" or hygroscopic micronized drugs are elevated. After the micronized powder has been elevated to the desired water content level, it is agglomerated. Non-hygroscopic materials must be bound with more traditional binders as described therein. Similarly, WO 95/105805 discloses a process for forming agglomerates where a mixture of homogeneous micronized materials are treated with water vapor to eliminate any convertible amorphous content which may destabilize at a later point. After treatment with water vapor, the now crystalline material is agglomerated. However, this application warns that if the vapor exposure is conducted after agglomeration, the product is "useless in an inhalation device."

The effect of moisture on the tableting characteristics of anhydrous lactose is discussed in Sebhatu, Elamin and Ahlneck, "Effect of Moisture Sorption on Tableting Characteristics and Spray Dried (15% Amorphous) Lactose," *Pharmaceutical Research*, Vol. 11, No. 9, pages 1233-1238 (1994). The article does not, however, discuss the formation of agglomerates, or the production of agglomerates which can yield an acceptable "fine particle fraction," also known as a "respirable fraction" when administered as part of oral inhalation therapy.

The Sebhatu et al. article uses a method for determining amorphous content which is more fully described by T. Sebhatu, M. Angberg and C. Ahlneck, "Assessment of the Degree of Disorder in Crystalline Solids by Isothermal Microcalorimetry," *International Journal of Pharmaceutics*, Vol. 104, pages 135-144 (1994). An isothermal microcalorimeter is used to determine the specific heat of crystallization for totally amorphous lactose, and then the "percent disorder" (denoted herein, for purposes of the present invention, "percent convertible amorphous content") is determined by dividing the specific heat of crystallization for a partially amorphous sample by the value previously obtained for the totally amorphous material, then multiplying by 100. The equipment described for making these measurements is satisfactory for use in the present invention.

SUMMARY OF THE INVENTION

The present invention provides an improved agglomerate and a process for making same. By design, the present invention takes advantage of the use of a solid binder in combination with fine drug particles and the amorphous characteristics which can be imparted to the solid binder and/or the drug. This occurs just when others would seek to eliminate such characteristics. The present invention also results in unique crystalline agglomerates of a first material and a solid binder which are free-flowing, sufficiently bulky and sufficiently stable to be handled, metered and delivered, even in extremely small doses. At the same time, the interparticulate bond strength of the agglomerates is sufficiently fragile to allow the agglomerates to break apart during administration through an inhaler so as to provide an acceptable fine particle fraction. All of this is accomplished substantially without the use of an additional, more conventional binder.

In particular, the present invention provides a process of producing agglomerates. The process includes providing particles of at least one first material, generally a pharmacologically active agent, and providing particles of at least one solid binder. At least one of these two particles, the drug or the solid binder, includes as part thereof, a preselected amount of a convertible amorphous content which is sufficient to, upon crystallization thereof allow for the formation of generally crystalline, agglomerates. The predetermined convertible amorphous content of the binder and/or the drug is capable of being converted to a crystalline form upon exposure to a preselected stimulus which includes, among other things, humidity.

The particles are then agglomerated while maintaining the preselected or predetermined amount of convertible amorphous content. After agglomeration is complete, the convertible amorphous content within the agglomerates is exposed to the preselected stimulus and is converted to a crystalline form. By "crystalline," it is understood that the agglomerates of the present invention can still contain some amorphous content, predominantly non-convertible amorphous phase with or without some amount of unconverted convertible amorphous content. The latter is to be minimized. Without wishing to be bound by any particular scientific theory, it is believed that the conversion of the convertible amorphous content creates crystalline bonds between the particles. These bonds are strong enough to preserve the integrity of the agglomerates during handling, storage and metering. However, they are soft enough to be overcome by commercially available inhalers so as to provide an acceptable fine particle fraction upon dosing.

It is an important aspect of the present invention that the agglomerates contain a certain content of convertible amorphous content during formation. "Convertible" means that the amorphous content, when exposed to certain predetermined or preselected stimuli, will convert from amorphous to crystalline form. This convertible amorphous content can be present as part of the drug, part of the solid binder, or both. The distribution of the amorphous content on the particles is generally unimportant so long as sufficient convertible amorphous content is present, preferably substantially homogeneously, throughout the system.

The fact that the solid binder may or may not contain any convertible amorphous content is not important in and of itself. In such instances, the solid binder still imparts certain advantageous properties to the resulting agglomerates in terms of their ability to flow freely, their bulk density, their strength and the ability to retard hang-up.

In a more preferred embodiment, the present invention provides a method of producing agglomerates of a pharmacologically active agent including the steps of providing of at least one pharmacologically active agent having an average particle size of below about 10 µm and at least one solid binder. Preferably, the majority of the solid binder also exists as particles of less than about 10 µm. Generally, the binder has a preselected amount of convertible amorphous content which is sufficient to allow for the formation of agglomerates with the pharmacologically active agent upon crystallization by exposure to a preselected stimulus such as atmospheric moisture. The next step involves forming a substantially homogeneous mixture of the particles while maintaining the preselected amount of convertible amorphous content. The mixture is then agglomerated while still maintaining the preselected amount of amorphous content. Finally, the convertible amorphous content of the solid binder and/or drug within the agglomerates is converted to a crystalline form by exposure to the preselected stimulus. The resulting agglomerates are free-flowing and are characterized by bridges or bonds between the particles such as, for example, between the pharmacologically active agent and the solid binder, (or even between the particles of the solid binder themselves), which are strong enough to withstand handling, but weak enough to allow for the delivery of an acceptable fine particle fraction of free particles of the pharmacologically active agent.

The result of this preferred aspect of the present invention is the creation of a dosage form of a pharmacologically active agent useful as part of oral and/or nasal inhalation therapy. The dosage form includes agglomerates of particles of the pharmacologically active agent and particles of crystalline solid binder. The particles preferably have an average particle size of 10 µm or less.

The ratio of drug to binder in the agglomerate can vary widely depending upon the amount of drug to be administered, the fine particle fraction desired and the amount of and relative distribution of, convertible amorphous content present as part of the drug and/or binder. In fact, the ratio of drug to binder can range from between about 1000:1 to 1:1000 (drug:binder). However, preferably, the drug and binder are present in a ratio of between 100:1 to 1:500 and even more preferably between 100:1 to 1:300.

The agglomerates generally range in sizes from between about 100 to about 1500 μm and an average size of between 300 and 1000 μm. The bulk density of the resulting agglomerates is between about 0.2 and about 0.4 g/cm$^3$. Preferably the ratio of drug to solid binder ranges from between about 20:1 to about 1:20 and most preferably 1:3 to 1:10. The agglomerates also preferably have an average size of between about 300 and about 800 μm and more preferably between about 400 and about 700 μm.

In another aspect of the present invention there is provided an intermediate agglomerate useful for producing a free-flowing crystalline agglomerate dosage form of a pharmacologically active agent. The intermediate agglomerate includes particles of a pharmacologically active agent and particles of solid binder, preferably anhydrous lactose. The binder and/or the drug particles include a preselected amount of convertible amorphous content which is sufficient to allow for the formation of crystalline agglomerates upon exposure to a preselected stimulus. The particles of pharmacologically active agent and particles of the binder have an average particle size of about 10 μm or below, and each is provided in a ratio of between about 100:1 and about 1:500 and even more preferably between about 100:1 and about 1:300. The resulting agglomerates range in size from between about 100 μm to about 1500 μm and have an average size of between 300 and 1000 μm. Their bulk density generally ranges from between about 0.2 and abut 0.4 g/cm$^3$.

These intermediate agglomerates are too weak to withstand normal handling and thus they are not suitable for a dosage form. They also have a relatively high rate of hang up in the nozzle of an inhaler. Such agglomerates are also not stable. Over time, they will convert, in an uncontrolled manner, to a crystalline form. This yields a higher level of variability in terms of bond strength and dosing uniformity. However, these amorphous agglomerates are very useful in the formation of crystalline dosage forms in which at least substantially all of the convertible amorphous content is converted to a crystalline form by exposure to a preselected stimulus.

A particularly preferred aspect of the present invention is the provision of a method of ensuring a higher level of dosing uniformity for very small doses of orally inhaled pharmacologically active agents or drugs (about 400 μg of drug or below). The method includes metering a dose of an agglomerated pharmacologically active agent as previously described and administering that dose of agglomerated pharmacologically active agent to a patient in need thereof.

The present invention also provides a metered dose of a pharmacologically active agent useful for administration by oral inhalation therapy. The metered dose can vary widely in size; including up to about 50,000 μg of the pharmacologically active agent per inhalation. The ability to accommodate such a wide range of dosing levels is a direct result of the advantages which inure from the use of the present invention to manufacture agglomerates. However, the present invention is most useful in the context of very small doses including up to about 400 μg of particulate pharmacologically active agent with the balance being lactose binder. More particularly, the dose contains about 100 μg of pharmacologically active agent or less. It is these smaller dosing levels which are the most demanding on dosage forms.

Oral inhalation of a pharmacologically active agent as previously noted, can be demanding, not only on dosing equipment, but also on formulations. The dosage form appears to need to simultaneously meet a number of criteria, many of which were thought to be mutually exclusive. For example, it is very important that the agglomerates be formed in a highly repeatable, consistent manner with very little variation in terms of size, drug content and interparticle bond strength. The agglomerates must also be sufficiently solid to allow them to be worked, sieved, spheronized and otherwise manipulated without failing apart. At the same time, the agglomerates must be sufficiently weak so as to allow them to break apart during inhalation and yield, to the extent possible, small, free particles of drugs in a manner which is therapeutically effective. For another example, the agglomerates must be sufficiently free-flowing to allow them to be loaded into an inhaler, and metered through the inhaler and delivered, with as little residue being retained as possible. However, forming agglomerates of inherently free-flowing materials can be difficult.

One of the most interesting aspects of the present invention is the realization that attempting to balance these often competing performance criteria is neither possible nor necessary. Instead, the invention uses certain properties when those properties are advantageous. Then, just when those same attributes would become liabilities, the agglomerate is changed fundamentally to eliminate those properties entirely. In their place, a new crystalline agglomerate is realized. This new agglomerate retains none of those properties of the former agglomerates which were useful for agglomerate formation, but detrimental to handling, measuring and administering.

Instead, the new agglomerates, after conversion of the convertible amorphous content of the solid binder and/or the drug, are free flowing and very consistent in terms of agglomerate size and size distribution. Furthermore, the agglomerates are sufficiently rugged to allow them to be handled, metered, and even dropped while within an inhaler without the adverse consequences found in the prior art. At the same time, when used in combination with an inhaler that can generate sufficient force, the structural integrity of these rugged agglomerates can be interrupted sufficiently so as to provide an acceptable fine particle fraction.

Figure 3:
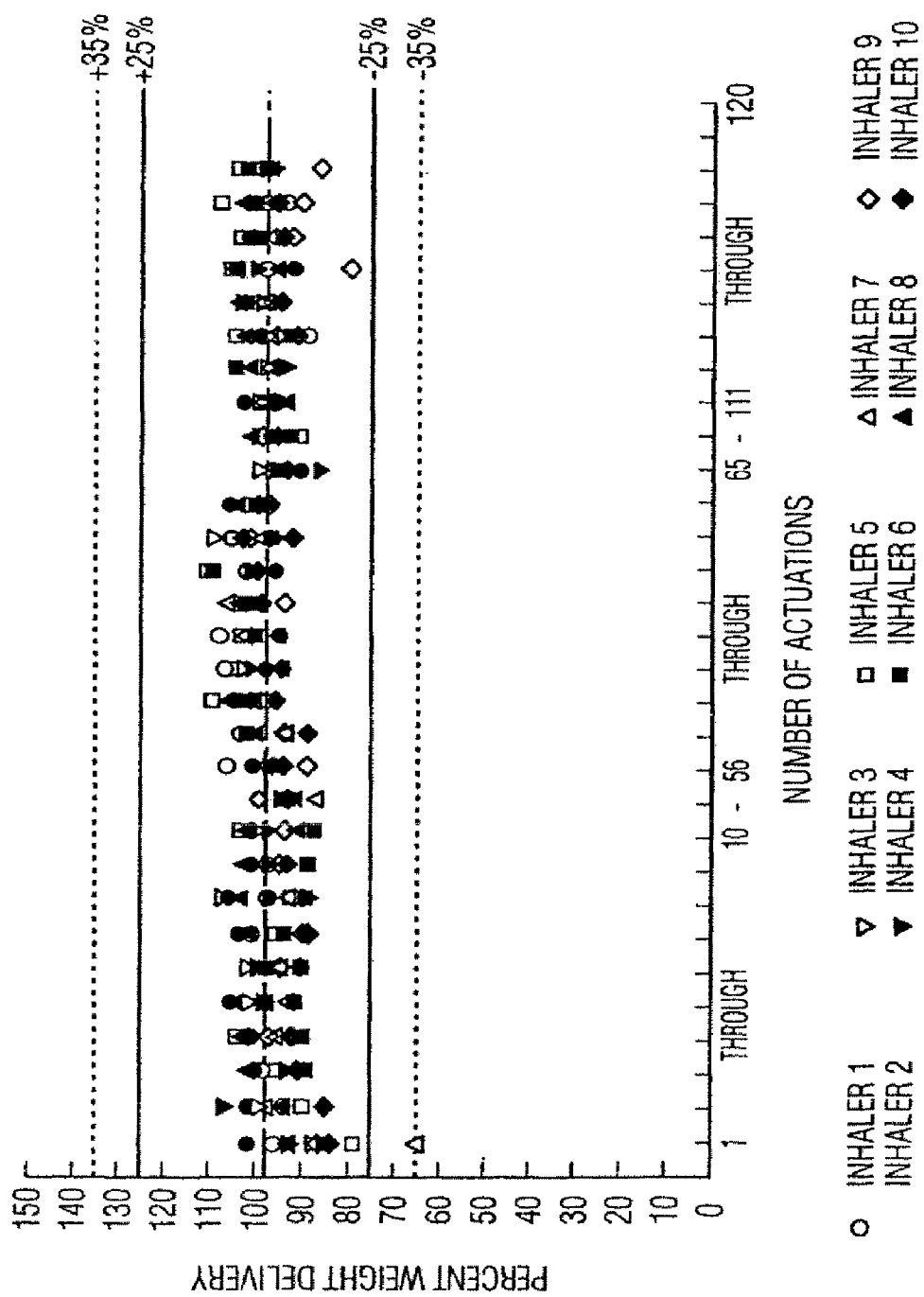

Therefore, in accordance with another aspect of the present invention, there is provided a crystalline agglomerate of a drug with an average particle size of 10 μm or less and particles of a solid binder. These particles are bound together as a result of the conversion at a portion of a convertible amorphous region of either the drug, the binder, or both. No additional binder is required. These agglomerates are provided in combination with a nasal or oral inhaler which is configured so as to provide a fine particle fraction of drug particles of at least 10%. In general, the agglomerates which result have a crush strength of between about 50 mg and about 5,000 mg. More preferably, the crystalline agglomerates in accordance with the present invention have a crush strength of between about 200 mg and about 1500 mg. Thus, the inhaler used for dosing these agglomerates will have to provide, as a minimum, sufficient force to overcome the inherent strength of the agglomerate so as to result in a fine particle fraction of at least about 10% or more. This means that at least 10% of the drug will be reduced to a fine particle fraction of particles having a size of 6.8 μm or less. It should come as no surprise that if an inhaler is configured to provide at least a 10% fine particle fraction of the drug when the agglomerate strength is 5,000 mg, the same inhaler will provide a much greater fine particle fraction if used in combination with agglomerates in accordance with the present invention having a strength of, for example, 500 mg.

It has also been found that by providing a solid binder having a similar range of particle sizes when compared to the particle size of the particles of drug, it is possible to obtain a substantially homogeneous distribution of drug in each metered dose, even when the metered doses of drug are as small as about 400 μg or below.

In sum, it has been found that by converting the amorphous content of the binder or drug to a crystalline form within the pre-formed agglomerate, once agglomeration is complete, one can impart desirable properties. When the amorphous content of the agglomerates is converted to crystalline form, the agglomerates become stable. They are, indeed, less sensitive to factors such as humidity and temperature. The crystalline material is also free-flowing and exhibits reduced hang up relative to the same agglomerates prior to conversion. It is easier to load into and empty from a dose hole and, therefore, provides for consistent metering. This coupled with high stability and homogeneity makes consistent dosing of very small doses possible.

Thus it has been found that, through the present invention, it is possible to provide materials which are ideally suited for agglomeration just when it is necessary to agglomerate such materials and it is also possible to produce agglomerates which are ideally suited for administering pharmacologically active substances through an oral inhalation system.

Another important aspect of the present invention is a change in the conventional perception of the amorphous content of particles. The industry has long known of the amorphous character imparted to certain materials by such processes as micronizing, spray drying, freeze drying and ball milling. Some degree of amorphous character is unavoidably imparted upon materials when the particle size is reduced using such techniques. However, because of the variability that can result from such amorphous materials, the industry has long sought a way to minimize or eliminate the creation of amorphous content during microparticle formation.

In fact, that is the very point of WO 95/05805. That PCT application seeks to form, as much as possible, a homogenous mixture of particles of as uniform characteristics as possible so as to insure the production of agglomerates having a more tightly controlled size. The theory appears to be that if one can insure a homogeneity in terms of particle size, mixture of particles and crystallinity, is easier to control the resulting size and composition of agglomerates. Therefore, moisture is added to the particles, prior to agglomeration, to insure that their entire convertible amorphous content is converted to crystalline form.

In accordance with the present invention, however, it has been found that the amorphous character of the drug and/or binder can be harnessed to the formulator's advantage. By using the amorphous content of the mixture as the binder, one can eliminate the need for additional binders. This can only be accomplished, however, where agglomeration occurs prior to exposure of significant quantities of atmospheric moisture. Once the particulate has been exposed to moisture, the conversion of the convertible amorphous content will prevent a solid state agglomeration and a formation of direct intercrystalline bonds.

Moreover, it has been found that merely imparting such amorphous content upon particles is not sufficient. Certainly, it has long been known to micronized drugs. However, because of many drugs' natural stability, they cannot be readily transformed to crystalline agglomerates as discussed herein. Rather, it has been discovered that by imparting a certain amount of amorphous character to a solid binder, a binder which is capable of being readily re-converted to a crystalline form, the advantages of the present invention can be realized. It has been discovered that the use of a solid metastable material as a binder provides advantages both when the binder is in its amorphous form and again when it is in its crystalline form, so long as the various forms are intentionally used at the right time.

BRIEF DESCRIPTION OF THE DRAWINGS

FIG. 1 is a graph illustrating the water uptake of agglomerates of the present invention when exposed to humidity before and after being subjected to conversion.

FIG. 2 is a block diagram illustrating a manufacturing scheme for agglomerates of either lactose alone or mometasone furoate and lactose.

FIG. 3 is a graph illustrating the results of a 122 cm (48 inch.) drop test wherein: ○ is inhaler 1, • is inhaler 2, ∇ is inhaler 3, ▼□ is inhaler 4, □□ is inhaler 5, ■ is inhaler 6, Δ is inhaler 7, ▲ is inhaler 8, ◇ is inhaler 9, and ♦ is inhaler 10.

Figure 4:
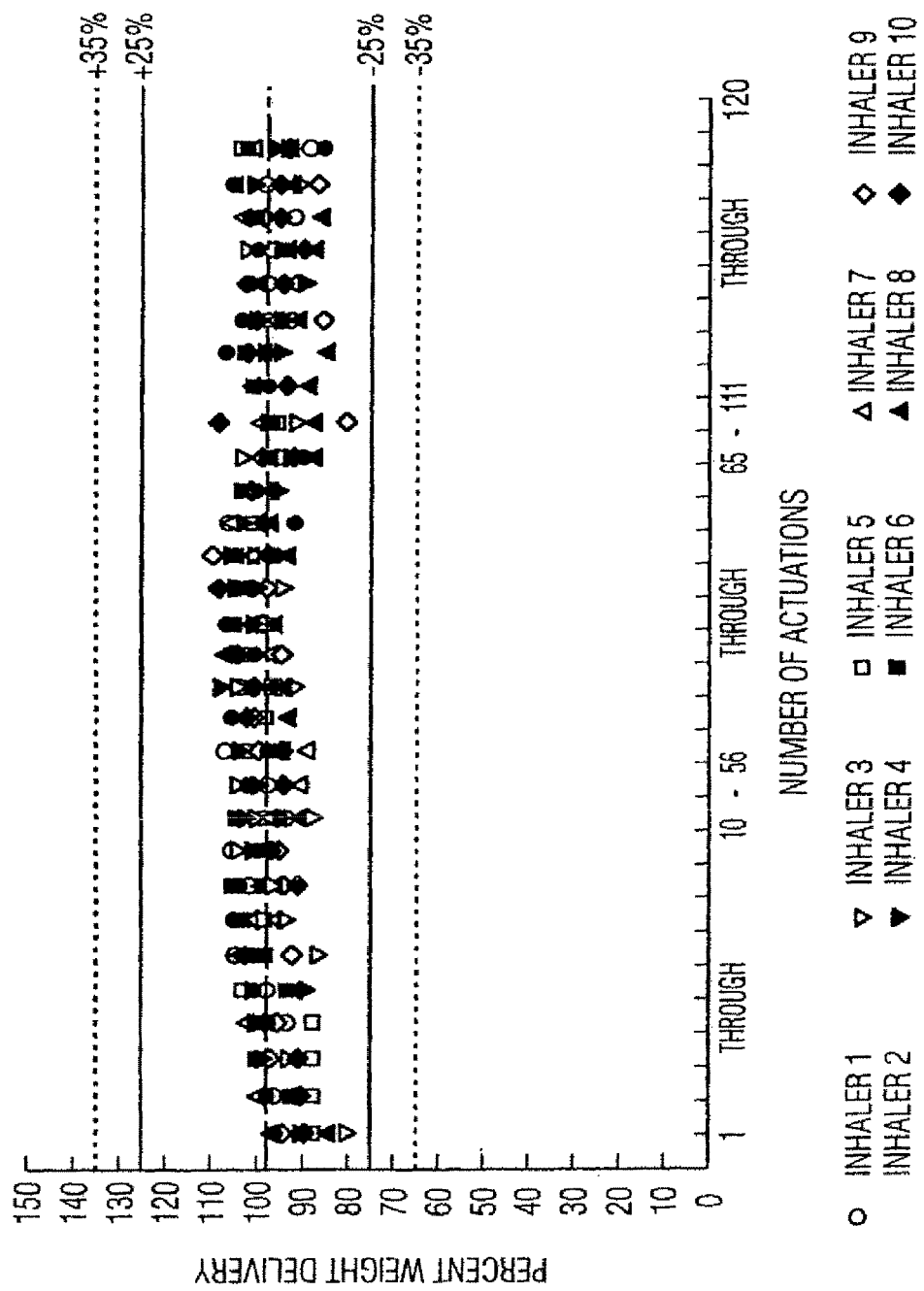

FIG. 4 is a graph illustrating the results of a control for a 122 cm (48 inch.) drop test wherein: ○ is inhaler 1, • is inhaler 2, ∇ is inhaler 3, ▼ is inhaler 4, □□ is inhaler 5, ■ is inhaler 6, Δ is inhaler 7, ▲ is inhaler 8, ◇ is inhaler 9, and ♦ is inhaler 10.

DETAILED DESCRIPTION OF THE INVENTION

An agglomerate in accordance with the present invention is a bound mass of small particulates. The agglomerates include at least one first material and at least one solid binder. The first material, in accordance with the present invention can be anything as, indeed, the present invention can be used broadly to make free-flowing agglomerates for any application including, medicine, cosmetics, food and flavoring, and the like. However, preferably, the first material is a pharmacologically active agent or drug which is to be administered to a patient in need of some course of treatment. The pharmacologically active agent may be administered prophylactically as a preventative or during the course of a medical condition as a treatment or cure.

Most preferably, in accordance with the present invention, the pharmacologically active agent or drug is a material capable of being administered in a dry powder form to the respiratory system, including the lungs. For example, a drug in accordance with the present invention could be administered so that it is absorbed into the blood stream through the lungs. More preferably, however, the pharmacologically active agent is a powdered drug which is effective to treat some condition of the lungs or respiratory system directly and/or topically. Particularly preferred pharmacologically active agents in accordance with the present invention include, without limitation, corticosteroids such as: mometasone furoate; beclomethasone dipropionate; budesonide; fluticasone; dexamethasone; flunisolide; triamcinolone; (22R)-6α,9α-difluoro-11β,21-dihydroxy-16α,17α-propylmethylenedioxy-4-pregnen-3,20-dione; tipredane and the like. β-agonists (including $\beta_1$ and $\beta_2$-agonists) including, without limitation, salbutamol (albuterol), terbutaline, salmeterol, and bitolterol may also be administered. Formoterol (also known as eformoterol) e.g., as the fumarate or tartrate, a highly selective long-lasting $\beta_2$-adrenergic agonist having bronchospasmolytic effect, is effective in the treatment of reversible obstructive lung ailments of various genesis, particularly asthmatic conditions. Another long-acting β-agonist which can be administered in accordance with the present invention is known as TA-2005, chemically identified as 2(1H)-Quinolinone, 8-hydroxy-5-[1-hydroxy-2-[[2-(4-(methoxyphenyl)-1-methylethyl]amino]ethyl]-monohydrochloride, [R-(R*,R*)]—also identified by Chemical Abstract Service Registry Number 137888-11-0 and disclosed in U.S. Pat. No. 4,579,854, the text of which is hereby incorporated by reference. Anticholinergics such as ipratropium bromide and oxitropium bromide may be used. So, too can sodium cromoglycate, nedocromil sodium and leukotriene antagonists such as zafirlukast and praniukast. Bambuterol (e.g. as hydrochloride), fenoterol (e.g. hydrobromide), clenbuterol (e.g. as hydrochloride), procaterol (e.g. as hydrochloride), and broxaterol are highly selective $\beta_2$-adrenergic agonists can be administered. Several of these compounds could be administered in the form of pharmacologically acceptable esters, salts, solvates, such as hydrates, or solvates of such esters or salts, if any. The term is also meant to cover both racemic mixtures as well as one or more optical isomers. The drug in accordance with the present invention can also be an inhalable protein or a peptide such as insulin, interferons, calcitonins, parathyroid hormones, granulocyte colony-stimulating factor and the like. "Drug" as used herein may refer to a single pharmacologically active entity, or to combinations of any two or more, an example of a useful combination being a dosage form including both a corticosteroid and a β-agonist. A preferred pharmacologically active agent for use in accordance with the present invention is mometasone furoate.

To be topically effective in the lungs or the upper and/or lower airway passages, it is important that the pharmacologically active agent be delivered as particles of about 10 μm or less. See Task Group on Lung Dynamics, Deposition and Retention Models For Internal Dosimetry of the Human Respiratory Tract, *Health Phys.*, 12, 173, 1966. The ability of a dosage form to actually administer free particles of these therapeutically effectively sized particles is the fine particle fraction. Fine particle fraction is, therefore, a measure of the percentage of bound drug particles released as free particles of drug having a particle size below some threshold during administration, Fine particle fraction can be measured using a multi-stage liquid impinger manufactured by Copley Instruments (Nottingham) LTD using the manufacturer's protocols. In accordance with the present invention, an acceptable fine particle fraction is at least 10% by weight of the drug being made available as free particles having an aerodynamic particle size of 6.8 μm, or less, measured at a flow rate of 60 liters per minute.

The amount of drug administered will vary with a number of factors including, without limitation, the age, sex, weight, condition of the patient, the drug, the course of treatment, the number of doses per day and the like. For mometasone furoate, the amount of drug delivered per dose, i.e. per inhalation, will generally range from about 10.0 μg to about 10,000 μg. Doses of 25 μg, 50 μg, 75 μg, 100 μg, 125 μg, 150 μg, 175 μg, 200 μg, 250 μg, 300 μg, 400 μg and/or 500 μg are preferred.

The drug may include some or all of the convertible amorphous content of the agglomerates as discussed herein.

The solid binder in accordance with the present invention can be any substance which can be provided in, or reduced to, a particle size which is roughly congruent with the size of the particles of the pharmacologically active agent as previously described. For example, agglomerates of mometasone furoate anhydrous USP will preferably be provided having particles of at least 80%≦5 μm and at least 95%≦10 μm (measured by volume distribution). The solid binder, such as anhydrous lactose, NF will be provided having particles of at least 60%≦5 μm, at least 90% under 10 μm, and at least 95%≦20 μm. The average particle size is roughly the same for both and is less than 10 μm.

When in a crystalline form, i.e. when all, or almost all of the convertible amorphous content of the solid binder converted to a crystalline form, the binder must be stable, capable of supporting and maintaining an agglomerate and binding particles of therapeutically active agents such that same can be released as a fine particle fraction of particles. The binder must also impart to the crystalline agglomerate a desired range of properties including bulk density, strength, a free-flowing character, and storage stability.

Preferably, the convertible amorphous content of the solid binder, if indeed, it contains some or all of the convertible amorphous content of the agglomerate, will convert from its amorphous form to its crystalline form upon exposure to a preselected or predetermined stimulus such as atmospheric moisture in the form of humidity. However, materials which meet all of the foregoing criteria and will convert responsive to other preselected stimuli such as, for example, temperature, radiation, solvent vapor and the like may also be used. Preferred solid binders include polyhydroxy aldehydes, polyhydroxy ketones, and amino acids. Preferred polyhydroxy aldehydes and polyhydroxy ketones are hydrated and anhydrous saccharides including, without limitation, lactose, glucose, fructose, galactose, trehalose, sucrose, maltose, raffinose, mannitol, melezitose, starch, xylitol, mannitol, myoinositol, their derivatives, and the like.

Particularly preferred amino acids include glycine, alanine, betaine and lysine.

Where the drug is completely crystalline, or where it contains only non-convertible amorphous content, the solid binder must provide all of the amorphous content of the agglomerate system and vice versa. Neither the solid binder material, nor the drug need naturally have such an amorphous content, so long as such an amorphous content can be reversibly imparted thereto.

It is possible that the drug, the binder or both contains a certain percentage of amorphous content which is non-convertible or stable under the conditions of use and storage, as well as when the preselected stimuli is applied. This stable amorphous content is not part of the convertible amorphous content previously discussed. As is generally the case, this stable amorphous content has some role in interparticulate binding. However, it will not contribute to the interparticulate bonding which results from the conversion between amorphous and crystalline materials in accordance with the present invention.

Therefore, in certain formulations such as those using, for example, mometasone furoate, all of the convertible amorphous content is contributed by the solid binder. As such, sufficient solid binder must be provided to impart enough convertible amorphous content to the agglomerate system. However, with another drug such as, for example, albuterol sulfate, which itself can contain convertible amorphous content, it may be possible to use a binder with no amorphous content or to use a mixture of a solid binder containing a certain lower percentage of amorphous content along with albuterol. Too much convertible amorphous content can result in agglomerates which are bound too tightly to yield the desirable fine particle fraction. Generally, the amount of amorphous content in the system should range from between about 1 to about 50% by weight and more preferably between about 3 and 30% by weight. Most preferably, the amount of convertible amorphous content in the system will range from between about 5 to about 25% by weight. Of course, it is equally acceptable to characterize the amorphous content of either the binder or the drug, individually, in terms of the percent of amorphous content in the system. Thus, where the binder contains the total convertible amorphous content and where the binder contains a 20% amorphous content and is provided in the 1:1 ratio by weight with the drug, the total convertible amorphous content in the system will be 10% by weight.

Some convertible amorphous character can be imparted upon certain material, during the course of reducing the particle size thereof. Thus, for example, if anhydrous lactose is micronized in a micronizer such as MICRON-MASTER® Jet Pulverizer available from the Jet Pulverizer Co., Palmyra, N.J., it is possible to obtain not only particles of the desired size, but also to impart a certain amount of amorphous content. This can also be accomplished using other traditional microparticle generating devices such as milling, spray drying or ball milling. See Briggner, Buckton, Bystrom and Darcy, "The use of isothermal microcalorimetry in the study of changes in crystallinity induced during the processing of powders," *International Journal of Pharmaceutics,* 105 (1994), pp. 125-135. However, where others have tried to minimize the degree of amorphous content generated and have considered this amorphous content to be an unfortunate, but generally unavoidable, side effect of particle size reduction, the present invention seeks to encourage a certain amount of amorphous content.

The present invention also seeks to control and maintain that amorphous character of the solid binder and/or the drug until a specified time in the agglomeration process. To this end, certain steps are taken to impart a preselected amount of amorphous character and to maintain the amorphous character of the solid binder and/or the drug. For example, when anhydrous lactose is pulverized using a Jet Pulverizer as previously discussed, pulverization is carried out under considerable pressure such as, for example, between about 50 and about 120 psig (3.45 to $8.27 \times 10^5$ newton/m$^2$). About 80-100 psig (5.51 to $6.89 \times 10^5$ newton/m$^2$) is preferred. The use of such high pressures results in a particularly violent particle formation environment and generally increases the amount of amorphous content. Moreover, applicants preferably use dry compressed nitrogen gas to pulverize the solid binder, as applicants have discovered that the exposure of the amorphous content to humidity during particle formation can act to reconvert the amorphous content back to a crystalline form prematurely.

Of course, it is also possible to impart an amorphous surface to particles of a solid binder and/or drug which is already of correct particle size or to use particulate which is inherently amorphous in character and can be converted to a crystalline form.

Once sufficient convertible amorphous content is present, that amorphous character must be maintained until such time as it is desirable to convert the particles into completely crystalline form. For solid binders or drugs, such as lactose, which are sensitive to humidity, this can be accomplished by processing and storing under low humidity conditions.

Preferably, the micronized materials are subsequently stored and/or processed under conditions of less than about 30% relative humidity ("RH") and more preferably, less than 20% RH at 21° C. By this it is meant that the micronized materials are processed and stored at an atmospheric moisture content which is equal to that of an atmosphere of 30% RH at 21° C., or less. Exact amounts of moisture present in the atmosphere at various temperatures can be derived from Table 5.27, "Mass of Water Vapor in Saturated Air," at page 5.150 of John A. Dean, *Lange's Handbook of Chemistry, Fourteenth Ed.*, McGraw-Hill, Inc. New York (1992). It is particularly preferable to store any materials containing convertible amorphous content under humidity conditions of less than 10% RH at 21° C. and, most preferably, as close to zero relative humidity as practicable. All processing may be carried out at any temperature. However, processing is usually more conveniently carried out between 0° C. and 38° C.

Generally, any method of agglomerating the solid binder and the pharmacologically active agent, which can be accomplished without converting the amorphous content of the solid binder to a crystalline form, prematurely, and which does not require the use of additional binder, can be practiced in accordance with the present invention. For this reason, one can generally not practice the agglomeration processes disclosed in the aforementioned U.S. Pat. No. 4,161,516 as water and/or moisture are added as a binder prior to agglomeration. This would cause the premature conversion of some or all of the amorphous content to a crystalline form which would actually retard agglomerate formation and lead to variability. This variability could also cause the formation of agglomerates which are too hard and strong. Even when such agglomerates are administered using an inhaler which provides a particularly violent dispensing action, these agglomerates may not yield an acceptable fine particle fraction.

It is important that the process produce agglomerates ranging in size from between about 100 to about 1500 μm. The agglomerates generally have an average size of between about 300 and about 1,000 μm. More preferably, the agglomerates have an average size of between about 400 and about 700 μm. Most preferably, the agglomerates will have an average size of between about 500 and 600 μm. The resulting agglomerates will also have a bulk density which ranges from between about 0.2 to about 0.4 g/cm$^3$ and more preferably, between about 0.29 to about 0.38 g/cm$^3$. Most preferably, the agglomerates will have a bulk density which ranges from between about 0.31 to about 0.36 g/cm$^3$.

It is also important to the dosing of the pharmacologically active agent that the agglomeration process yield a relatively tight particle size distribution. In this context, particle size refers to the size of the agglomerates. Preferably, no more than about 10% of the agglomerates are 50% smaller or 50% larger than the mean or target agglomerate size. Thus for a desired agglomerate of 300 μm, no more than about 10% of the agglomerates will be smaller than about 150 μm or larger than about 450 μm.

A preferred method of preparing the agglomerates in accordance with the invention which meets all of the foregoing criteria involves mixing preselected amounts of one or more pharmacologically active agent(s) and the micronized, amorphous content containing, dry solid binder in a ratio of between about 100:1 and about 1:500 and even more preferably between about 100:1 and about 1:300 (drug:binder) and preferably a ratio of between 20:1 to about 1:20. Most preferably, the drug would be provided in an amount of 1:3 to about 1:10 relative to the amount of the solid binder.

These particles are then preferably mixed in some form of mechanical mixing device. Preferably, mixing will result in substantial homogeneity. Of course, it may not be possible for one to obtain absolute homogeneity. However, a tolerance of ±10% is acceptable during blending and ±5% is acceptable during agglomeration. Blending such ingredients, in fine particle form, may be a challenge in and of itself. Blending can be accomplished, for purposes of example only, using a Patterson-Kelly V-shape blender having a pin intensifier bar. Preferably, the blending procedure is carried out in the clean room, and, as previously noted, the humidity and temperature of the room should be controlled. At 21° C. and 20% RH for example, conversion of the amorphous content is sufficiently slow to allow blending. Depending upon the size of the batch, blending can be accomplished within between about 3 and 15 minutes total. If the mixture of micronized drug and solid binder will not be further processed immediately, it should again be stored under low humidity and low temperature conditions.

For a particularly small amount of drug as relative to the solid binder, the conventional blending technique may not result in an acceptably homogeneous mixture. In this case, the following approaches may be used:
(1) blending of the drug or drugs and the solid binder before micronization;
(2) when a mixture of pharmacologically active agents is used, and particularly when one is present in significantly larger amounts than the other, blending the two agents together, micronizing the blend and then blending with micronized solid binder having a convertible amorphous content; and/or
(3) forming microspheres by spray drying, such as: (a) dissolving or suspending the drug in an aqueous solution of a diluent or carrier, such as lactose, spray drying and then mixing the resulting microspheres with micronized solid binder having a convertible amorphous content; or (b) spray drying a nonaqueous solution or suspension of drug, containing suspended, micronized diluent or carrier particles, such as lactose, then mixing with solid binder particles having a convertible amorphous content. In fact, even with larger amounts of drug, it may be desirable to employ the first approach.

From the blender, the mixed particles are poured into a conventional screen/pan combination for agglomerate formation. The particles can now be thought of as an agglomeration as they no longer retain as much of their individual identity. They are not "agglomerates" as described herein as they are not smaller, individualized collections of particles of generally spherical shape and/or greater density.

Screen and pan are then rotated in an eccentric circular motion in a plane parallel to the ground. This can be done manually or using a screen shaking device. An intermittent tapping is applied perpendicularly to the top of the pan which forces or meters materials through the screen into the pan below where the eccentric motion of the pan encourages agglomerate formation as defined previously. The agglomerates are also simultaneously spheronized. Of course, this agglomeration procedure, as with any agglomeration procedure in accordance with the present invention, must be carried out under low humidity conditions to prevent the unwanted, premature conversion of the amorphous content of the solid binder to crystalline form.

After the agglomerates are formed and properly sized by, for example, pouring through another screen, they can be exposed to a preselected stimuli, such as higher humidity, to cause the substantially complete conversion of the convertible amorphous content contained within the agglomerates to a crystalline form.

Of course, the higher the humidity, the less the amount of time necessary for exposure. However, a somewhat gradual and controlled conversion is preferred as the strength of the agglomerates is to be tightly controlled. Agglomerates containing convertible amorphous content can be exposed to relative humidity of between about 30% and about 80% (at 25° C.) for a time period which is sufficient to convert the entire amorphous content. More preferably, the convertible amorphous content is converted by exposure to an atmosphere having a water content equal to a relative humidity of between about 40% and about 60% (measuring the relative humidity at about 25° C.). This is particularly useful when the solid binder is anhydrous such as anhydrous lactose. The amount of time can vary dramatically with the size and density of the agglomerates and the surface area of exposure. For example, placing a thin layer of agglomerates on a flat open tray will yield a much faster conversion overall than placing the same quantity of agglomerate in a narrow jar. In certain cases, the length of exposure need be on the order of tens of minutes. In other instances, one to two days may be required.

Because, preferably, the exposure is controlled to relative humidities of 65% or below (at 25° C.), there is relatively little concern about overexposure. So long as sufficient time is provided to allow all of the convertible amorphous content of the agglomerates to convert to crystalline form, the fact that additional exposure may take place is generally not of any consequence. If humidity levels above about 65% are used, however, then the water vapor can actually act as a binder. While the use of water as a binder is well known, it is detrimental to the ability to generate a fine particle fraction, particularly when used in combination with the principal mode of binding described herein; namely crystalline binding. Therefore, it is still desirable to limit the exposure of the agglomerates to elevated humidity levels beyond the point necessary for complete conversion. After conversion, the agglomerates have an interparticulate bonding strength which is measurably greater than the interparticulate bonding strength prior to conversion.

The agglomerates that result are, as previously described, generally crystalline in nature, free-flowing, rugged and resistant to hang up. These agglomerates can be stored, handled, metered and dispensed while maintaining their structural integrity. The agglomerates also have a very desirable and consistent size and size distribution. Perhaps most importantly, the crystalline agglomerates of the present invention have sufficient strength to allow them to be handled and abused. At the same time, the agglomerates remain soft enough to be broken sufficiently during dosing so as to provide an acceptable fine particle fraction. In general, the agglomerates have a strength which ranges from between about 50 mg and about 5,000 mg and most preferably between about 200 mg and about 1,500 mg. The crush strength was tested on a Seiko TMA/SS 120C Thermomechanical Analyzer available from Seiko Instruments, Inc. Tokyo, Japan, using procedures available from the manufacturer. It should be noted that strength measured in this manner is influenced by the quality and extent of the interparticulate crystalline bonding described herein. However, the size of the agglomerates also plays a role in the measured crush strength. Generally, larger agglomerates require more force to crush than do the smaller particles.

When agglomerates produced in accordance with the protocol reported in Example 1 were dosed at 100 µg per inhalation using a powder inhaler as described in WO 94/14492 assigned to Schering Corporation, sufficiently violent force was generated so as to break up the agglomerates enough to yield the desired level of free drug particles having a size of about 6.8 µm or less. Of course, the degree of force which must be generated while the agglomerates are dispensed is dependent upon the internal bond strength of the agglomerates. The greater the bond strength, the greater the amount of force which will be required to yield an acceptable fine particle fraction. The agglomerates of the present invention, while too strong and stable for certain inhalers are, nonetheless, useful in other commercially available inhalers and, when dispensed from same, an acceptable fine particle fraction results. Such inhalers include, without limitation, Schering's inhaler as identified above, Diskhaler (Allen & Hanburys), Accuhaler (Allen & Hanburys), Diskus (Glaxo), Spiros (Dura), Easyhaler (Orion), Cyclohaler (Pharmachemie), Cyclovent (Pharmachemie), Rotahaler (Glaxo), Spinhaler (Fisons), FlowCaps (Hovione), Turbospin (PH&T), Turbohaler (Astra), EZ Breath (Norton Healthcare/IVAX) MIAT-HALER (Miat), Pulvinal (Chiesi), Ultrahaler (Fisons/Rhone Poulenc Rorer), MAG-Haler (GGU), Prohaler (Valois), Taifun (Leiras), JAGO DPI (JAGO), M L Laboratories' DPI (M L Laboratories).

The inhaler must be capable of producing sufficient force to break up whatever agglomerate is used so as to produce an acceptable fine particle fraction. Therefore, an agglomerate having a crush strength of 1,000 mg as measured in the manner described herein, must be used in combination with an inhaler that can apply sufficient force to ensure that at least a 10% fine particle fraction results from each dose therefrom.

As shown in FIG. 1, mometasone:anyhydrous lactose agglomerates of a ratio of 1:5.8 (by weight) were exposed to 50% relative humidity at 25° C. both before and after conversion. The graph using the unbroken line (I) demonstrates the moisture uptake of the agglomerates when exposed to humidity before the agglomerates are converted to crystalline form. Moisture is absorbed very quickly reaching a maximum point. At that point, conversion to the crystalline form takes place. As the result of that conversion, water is actually expelled and the overall moisture content drops By the same token, once agglomerates which have been converted are exposed to moisture, they may absorb a small amount of moisture, but thereafter, moisture uptake is flat. See broken line (II). Amongst other things, FIG. 1 demonstrates the resulting stability of the agglomerates which are formed in accordance with the present invention.

The discovery and use of the increasing bond strength of the crystalline agglomerates is significant for a number of reasons. First the resulting agglomerates are free-flowing, stable, and able to be handled and packaged appropriately. Second, the agglomerates provide the necessary homogeneity and bulk density to allow them to be consistently loaded into the dose hole of an inhaler, even in particularly small doses. Thus the crystalline agglomerates can be accurately metered, measured and delivered. This is aptly demonstrated in FIG. 2. When the process of the present invention was carried out on lactose alone, and when humidity was added to the lactose prior to agglomeration, the resulting lactose agglomerate proved to be too soft to handle. Significant problems in repeatable dosing would thus be realized. These same results were observed when mixtures of drug and lactose were exposed to humidity prior to agglomeration.

In fact, in formulating a batch in accordance with the present invention as described in Example 1, anhydrous lactose was used that had already been converted. That fact was not known at the time. When the resulting agglomeration protocol did not yield the desired results, the cause was investigated. The prior conversion of the lactose was subsequently discovered. Thus, it is important to maintain the convertible amorphous content of the drug and/or binder in that state until after the formation of agglomerates as described herein.

Figure 2:
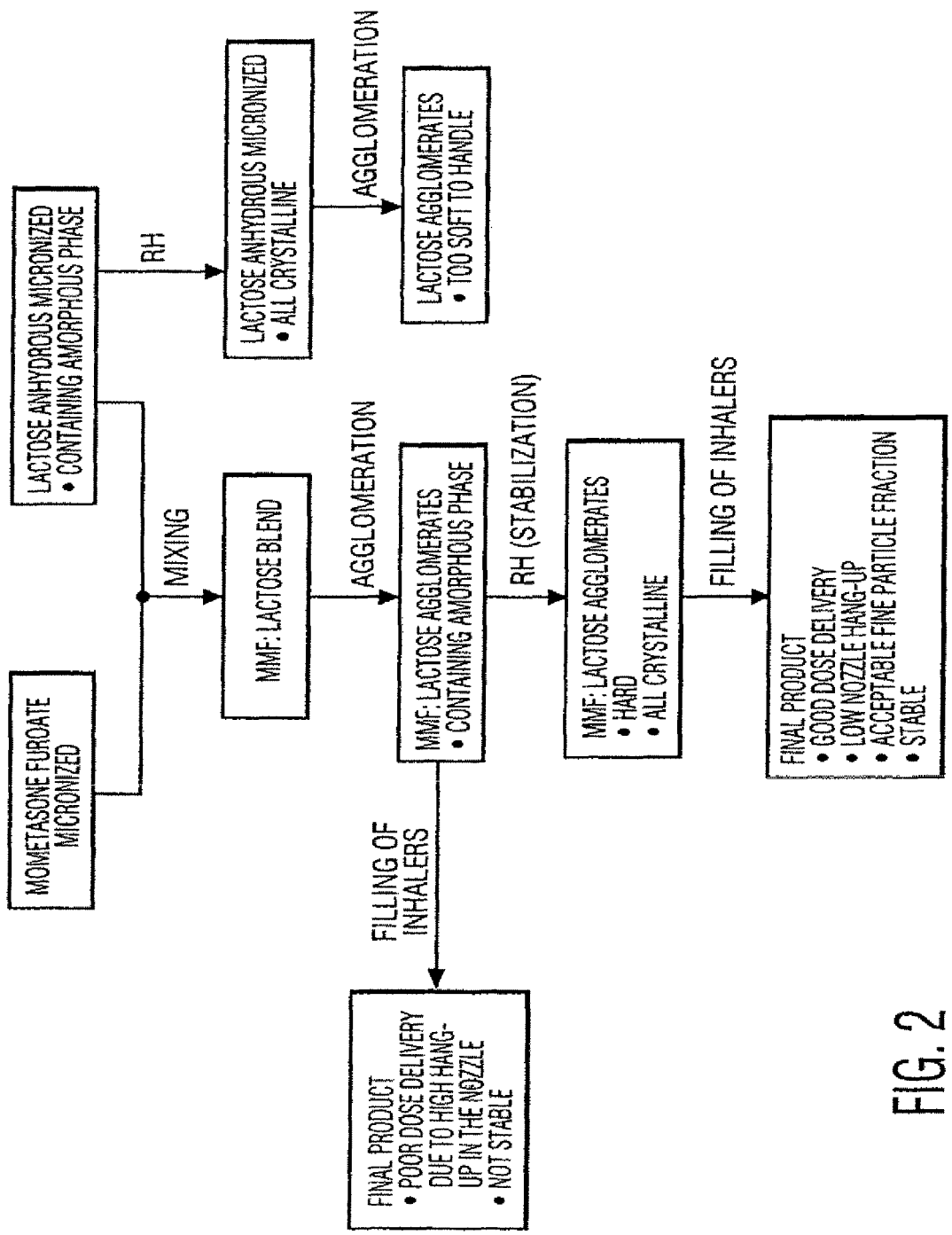

In another experiment also illustrated in FIG. 2, mometasone containing agglomerates were filled into an inhaler prior to stabilization with humidity. The final product was not stable and provided poor dose delivery due to high hang up in the nozzle of the inhaler and elsewhere. When the same drug containing agglomerates were stabilized by exposure to humidity as discussed herein, the resulting agglomerates were hard, free-flowing and easily handled. The internal bond strength was increased, allowing for proper handling characteristics. Yet the agglomerates remained soft enough to yield an acceptable fine particle fraction.

The present invention results in a higher degree of dosing uniformity. As shown in Table 1, agglomerates produced in accordance with the present invention were loaded into 10 inhalers as described in the aforementioned WO 94/14492. The inhalers were set to deliver 100 µg of mometasone furoate per inhalation. Mometasone furoate was provided in a ratio of 1:5.8 to anhydrous lactose (680 µg total agglomerate) and were produced as described in Example 1.

TABLE 1

Dose Uniformity Over the Labeled Number Of Inhalations (Emitted Dose)

| Inhaler Number | Initial Unit Dose Inhalation 1 (μg) | Middle Unit Dose Inhalation 60 (μg) | Final Unit Dose Inhalation 120 (μg) |
| --- | --- | --- | --- |
| 1 | 91 | 101 | 98 |
| 2 | 91 | 96 | 93 |
| 3 | 99 | 89 | 90 |
| 4 | 88 | 100 | 100 |
| 5 | 105 | 100 | 96 |
| 6 | 95 | 95 | 96 |
| 7 | 106 | 106 | 96 |
| 8 | 92 | 96 | 89 |
| 9 | 109 | 100 | 93 |
| 10 | 90 | 95 | 100 |
| Average | 97 | 98 | 95 |
| % CV ** | 7.9 | 4.7 | 4.0 |

* Ideal dose is 100 μg
** Percent Coefficient of Variation

The emitted dose was determined using a Dosage Unit Sampling Apparatus for Dry Powder Inhalers similar to that described in *Pharmaceutical Forum*, Vol. 20, No. 3, (1994) pp. 7494. The emitted dose was collected using a separatory funnel attached at one end to a sintered glass fitter at an air flow rate of 60 L/minute for a total of 4 seconds. The drug was then dissolved in a solvent and analyzed using HPLC as is known in the art. It is clearly evident from a review of Table 1 that from a first inhalation dose, through the 120th, there is great consistency. In addition, the consistency from inhaler to inhaler is significantly higher than one would normally expect. Perhaps most importantly, the average over all 120 doses for 10 inhalers shows great consistency. These numbers also indicate that very little material is lost during dosing. Thus, hang-up and dosing problems resulting from filling the dosing hole are minimized.

The fine particle fraction (as a percentage of the total dose) resulting from these emitted doses was also tested (Table 2). The fine particle fraction (≦6.8 μm) was determined at a 60 L/minute flow rate using a multi-stage (5-stage) liquid impinger manufactured by Copley Industries (Nottingham) LTD.

TABLE 2

| Inhaler Number | Initial Unit Dose Inhalation 1 | Middle Unit Dose Inhalation 60 | Final Unit Dose Inhalation 120 |
| --- | --- | --- | --- |
| 1 | 28 | 24 | 25 |
| 2 | 19 | 21 | 22 |
| 3 | 27 | 25 | 22 |
| Average | 24 | 23 | 23 |

The measured fine particle fraction from each inhaler was greater than 10% and, in addition, was greatly uniform from the first dose through dose 120.

A multi-stage impinger allows one to measure the fraction of certain sized particles in each of its various stages. As illustrated in Table 3, there is great uniformity between dose 1 and dose 120 in terms of the cumulative fine particle fraction which are less than the 13 μm, less than 6.8 μm, less than 3.1 μm and less then 1.7 μm.

TABLE 3

| Particle size (μm) | Initial Dose* Inhalation 1 | Middle Dose* Inhalation 60 | Final Dose* Inhalation 120 |
| --- | --- | --- | --- |
| <13.0 | 28 | 26 | 26 |
| <6.8 | 24 | 23 | 23 |
| <3.1 | 15 | 16 | 16 |
| <1.7 | 7 | 8 | 8 |

*Average of three determinations.

Finally, as shown in FIGS. 3 and 4, the agglomerates of the present invention are very durable. FIG. 4 illustrates the control. In this case, it illustrates, graphically, the percent of weight delivered or the emitted dose, in weight percent, of 10 inhalers over 120 doses each. The inhalers used were the Schering powder inhaler previously identified and the doses were 100 μg of mometasone furoate with an anhydrous lactose binder produced as described in Example 1. FIG. 3 presents the same data, for identically configured inhalers, after they had been dropped onto a hard surface from a height of about 122 cm (48 inches). A comparison of the results memorialized in FIGS. 3 and 4 show that very little change is exhibited overall.

The present invention helps ensure an unprecedented degree of agglomerate uniformity which significantly reduced the variability of dosing as previously demonstrated. For example, if moisture is added prior to or during agglomeration, a certain percentage of the solid binder will begin to convert to a crystalline form. The degree of crystal formation can vary greatly from particle to particle. As a result, the size of the agglomerate and the physical strength of the interparticulate bonding can vary greatly. In addition, the binder can actually begin to dissolve and this would create bonds which are too strong. This immediately translates into dose variability during inhalation and a variability in the terms of the fine particle fraction of drug delivered. The present invention overcomes this problem and efficiently provides uniform agglomerates which are easy to produce, store, handle and administer.

EXAMPLES

Example 1

To ensure the quality and uniformity of the product, the environmental conditions for handling and manufacturing agglomerates in accordance with the present invention were as follows:

Micronization of mometasone and lactose: 21° C.±2° and 20% RH±5%

Storage of micronized lactose: 21° C.±2° and less than 15% RH

Powder blending and agglomeration: 21° C.±2° and 20% RH±5%

Conversion of powder agglomerates: 25° C.±2° and 50% RH±5%

A Patterson-Kelley V-shape blender installed with a pin intensifier bar was set-up in a clean room with temperature and humidity controlled at 21° C. and 20% RH, respectively. Half of the micronized lactose anhydrous was charged into the V-blender. The micronized mometasone furoate anhydrous was added next. Then, the balance of the micronized lactose anhydrous was added.

The V-blender was turned on for 5 minutes at a rotation speed of about 24 RPM. Next, the V-blender was rotated for 3 minutes with the pin intensifier bar turned on for the first 1 minute at a pin tip speed of about 9 meters/second. The blending protocol was then repeated.

Samples were taken from right, left, and bottom of the V-blender to test the blend uniformity using a unit-dose sampling thieve.

To agglomerate this mixture, a screen shaker was set up in a clean room with temperature and humidity controlled at 21° C. and 20% RH, respectively. Thirty (30) mesh screens, pans, and stainless-steel containers were washed with 70% alcohol and dried.

Screen/pan combinations were assembled and placed on the shaker. Into each 12 inch, 30 mesh screen/pan set, 200 g of the mometasone:anhydrous lactose blend in a ratio of 1:5.8 (drug:binder) was added. The powder blend was spread on the screen so that the level of the powder blend was lower than the edge of the sieve frame. The screen/pan was placed on the sieve support plate of the shaker. A stainless-steel sieve cover was placed on the top screen.

The timer was then set for 10 minutes and the device was turned on such that an eccentric circular shaking with a one inch eccentric orbit at a speed of about 280 rpm occurred. The screen/pan was also tapped at a rate of 150 taps/minute to meter material through the screen. The process was stopped and multiple pans consolidated.

The agglomerates formed were poured onto a 20 mesh screen and the screen was tapped lightly. The material retained on the 20 mesh screen was discarded.

The agglomerates which passed through the 20 mesh screen were stored in the suitable containers.

When ready to convert the material, the agglomerates were spread onto a stainless-steel tray and exposed in a clean room having a temperature and humidity controlled at 25° C. and 50% RH, for 24 hours. The agglomerates were then combined and placed in a suitable container.

The bulk density was determined using a Vanderkamp Tap Density Tester set for one tap. Particle size distribution of the agglomerates was determined using a Malvern 2605L particle size analyzer.

Example 2

Three additional batches were produced in accordance with the process generally described in Example 1. The batch size and drug to binder ratios are illustrated below in Table 4:

TABLE 4

REPRODUCIBILITY OF MOMETASONE: LACTOSE AGGLOMERATES

| BULK SIZE | MMF: LACTOSE RATIO | BULK DENSITY ($g/cm^3$) | PARTICLE SIZE DISTRIBUTION DIAMETER (μm) UNDER 10% | 50% | 90% | mean |
|---|---|---|---|---|---|---|
| 0.75 Kg | 1:5.8 | 0.35 | 420 | 540 | 790 | 580 |
| 9.60 Kg | 1:5.8 | 0.35 | 370 | 510 | 740 | 540 |
| 9.60 Kg | 1:19 | 0.35 | 390 | 540 | 770 | 570 |

As will be readily appreciated, despite varying ratios of binder and drug, as well as varying batch sizes, a high degree of repeatability was observed in terms of bulk density and particle size distribution. Particle size in this context refers to the size of the agglomerate rather than that of the particulate binder and/or drug.

What is claimed is:

1. A uniform dry powder composition comprising crystalline agglomerates of fine particles of at least one pharmacologically active agent and particles of lactose wherein the composition has a bulk density of from about 0.29 to about 0.38 $g/cm^3$, and wherein the composition is substantially homogeneous; wherein said at least one active agent comprises mometasone furoate.

2. A composition according to claim 1, wherein the composition has a bulk density of from about 0.31 $g/cm^3$ to about 0.38 $g/cm^3$.

3. A composition according to claim 1, wherein the composition has a bulk density of from about 0.35 $g/cm^3$ to about 0.38 $g/cm^3$.

4. A composition according to claim 1, wherein the composition has a bulk density of about 0.35 $g/cm^3$.

5. A composition according to claim 1, wherein the mometasone furoate and lactose particles have a particle size of less than about 10 μm.

6. A composition according to claim 1, wherein the mometasone furoate particles and lactose particles have a particle size of from about 5 μm to about 10 μm.

7. A composition according to claim 1, wherein the mometasone furoate particles and lactose particles have a particle size of from about 5 μm to about 6.8 μm.

8. A composition according to claim 1, wherein the mometasone furoate particles and lactose particles have a particle size of about 4.7 μm.

9. A composition according to claim 1, wherein the mometasone furoate and lactose particles have a particle size of less than 6.8 μm.

10. A composition according to claim 1, wherein the mometasone furoate is anhydrous mometasone furoate.

11. A composition according to claim 1, wherein the lactose is anhydrous lactose.

12. A composition according to claim 1, wherein the lactose is hydrous lactose.

13. A composition according to claim 1, wherein the agglomerates have an average size of from about 300 μm to about 1000 μm.

14. A composition according to claim 1, wherein the agglomerates have a average size of from about 400 μm to about 700 μm.

15. A composition according to claim 1, wherein the agglomerates have a average size of from about 500 μm to about 600 μm.

16. A uniform dry powder composition comprising agglomerates having an average size of from about 300 μm to about 1000 μm; said agglomerates comprising fine particles of mometasone furoate and particles of lactose wherein the composition has a bulk density of from about 0.29 to about 0.38 $g/cm^3$, and wherein the composition is substantially homogeneous.

17. A composition according to claim 16, wherein the agglomerates have a average size of from about 500 μm to about 600 μm.

18. A composition according to claim 16, wherein the powder comprises crystalline agglomerates.

19. A uniform dry powder composition comprising agglomerates having an average size of from about 300 μm to about 1000 μm; said agglomerates comprising fine particles of at least one pharmacologically active agent comprising mometasone furoate and particles of lactose wherein the composition has a bulk density of from about 0.29 to about 0.38 $g/cm^3$, and wherein the composition is substantially homogeneous.

20. A composition according to claim 19, wherein the agglomerates have a average size of from about 500 μm to about 600 μm.

21. A composition according to claim 19, wherein the powder comprises crystalline agglomerates.

22. A process for preparing a uniform dry powder composition comprising crystalline agglomerates of fine particles of one pharmacologically active agent which is mometasone furoate and particles of lactose wherein the composition has a bulk density of from 0.29 to 0.38 g/cm$^3$ and the composition is substantially homogeneous, the process comprising:

(a) micronizing particles of mometasone furoate and particles of lactose, so that at least one of the mometasone furoate and the lactose has a preselected amount of convertible amorphous content which is capable of being converted to crystalline form upon exposure to a preselected stimulus, the convertible amorphous content being provided in an amount which is sufficient to allow for the formation of agglomerates;

(b) agglomerating the particles of mometasone furoate and lactose while maintaining the preselected amount of convertible amorphous content; and (c) exposing the convertible amorphous content within the agglomerates to the preselected stimulus to convert the convertible amorphous content to a crystalline form.

23. A process according to claim 22 wherein the stimulus is an atmosphere having a humidity sufficient to cause substantially complete conversion of the convertible amorphous content within the agglomerates to a crystalline form.

24. A composition according to claim 22, wherein the agglomerates have an average size of from about 300 μm to about 1000 μm.

25. A process for preparing a uniform dry powder composition comprising agglomerates of fine particles of one pharmacologically active agent which is mometasone furoate and particles of lactose wherein the composition has a bulk density of from 0.29 to 0.38 g/cm$^3$ and the composition is substantially homogeneous, the process comprising:

micronizing particles of mometasone furoate and particles of lactose to obtain micronized mometasone furoate particles and lactose particles, wherein at least one of mometasone furoate and the lactose has a convertible amorphous content;

mixing the micronized mometasone furoate particles and lactose particles to obtain a substantially homogenous mixture, and agglomerating the mixture and maintaining the convertible amorphous content; and spheronizing the agglomerates, and exposing the convertible amorphous content within the agglomerates to an atmosphere having a humidity sufficient to cause substantially complete conversion of the convertible amorphous content within the agglomerates to a crystalline form.

* * * * *